(12) United States Patent
Prezelin et al.

(10) Patent No.: US 11,185,435 B2
(45) Date of Patent: Nov. 30, 2021

(54) BAG FOR COLLECTING URINE

(71) Applicant: B. Braun Medical SAS, Boulogne Billancourt (FR)

(72) Inventors: Anthony Prezelin, Nogent-le-Rotrou (FR); Laura Blocquel, Nogent-le-Rotrou (FR)

(73) Assignee: B. Braun Medical SAS, Saint-Cloud (FR)

( * ) Notice: Subject to any disclaimer, the term of this patent is extended or adjusted under 35 U.S.C. 154(b) by 0 days.

(21) Appl. No.: 14/902,362

(22) PCT Filed: Sep. 2, 2014

(86) PCT No.: PCT/EP2014/002376
§ 371 (c)(1),
(2) Date: Feb. 17, 2016

(87) PCT Pub. No.: WO2015/000602
PCT Pub. Date: Jan. 8, 2015

(65) Prior Publication Data
US 2016/0206469 A1    Jul. 21, 2016

(30) Foreign Application Priority Data

Jul. 2, 2013    (FR) ...................................... 1301561

(51) Int. Cl.
*A61F 5/451*    (2006.01)
*A61F 5/44*    (2006.01)
(Continued)

(52) U.S. Cl.
CPC ............ *A61F 5/451* (2013.01); *A61F 5/4404* (2013.01); *A61F 5/4405* (2013.01); *A61M 25/002* (2013.01); *A61M 27/00* (2013.01)

(58) Field of Classification Search
CPC ...................... A61F 5/44; A61F 5/4405; A61F 5/4404–443; A61F 5/451–4556; A61M 25/002; B65D 75/008
See application file for complete search history.

(56) References Cited

U.S. PATENT DOCUMENTS 2,856,932 A    10/1958    Griffitts
3,762,399 A    10/1973    Riedell
(Continued)

FOREIGN PATENT DOCUMENTS

DE    2227416 A1    12/1972
DE    102007018275 A1    3/2008
(Continued)

OTHER PUBLICATIONS

International Search Report and Written Opinion for International Patent Application No. PCT/EP2014/002376, dated Nov. 3, 2014 (11 pages).

*Primary Examiner* — Tatyana Zalukaeva
*Assistant Examiner* — Meagan Ngo
(74) *Attorney, Agent, or Firm* — Clark & Elbing LLP

(57) ABSTRACT

The purpose of the invention is to create a urine bag that can be easily folded in order to occupy less space prior to use and that can be easily manipulated by a patient, in particular a paraplegic patient. This is achieved using a urine collection bag (1) formed by two sheets of plastic material that are stacked and welded along the periphery (2) thereof. The collection bag (1) comprises a collection compartment (3), said inlet being in communication with the intake port (4) and delimiting the upper portion of the collection compartment (3). The intake port (4) is provided with a vertical extension (8) closed along their periphery (22) thereof and comprising a urinary catheter (9). The bag (1) of the invention is characterised in that the intake port (4) and the inlet (Continued)

(6) are offset vertically, and in that the vertical height (ho) of the bag (1) corresponds to a multiple of the height (hp) of the extension (8).

11 Claims, 2 Drawing Sheets

(51) Int. Cl.
   *A61M 25/00* (2006.01)
   *A61M 27/00* (2006.01)

(56) References Cited

U.S. PATENT DOCUMENTS

| | | | | |
|---|---|---|---|---|
| 4,000,649 | A * | 1/1977 | Hanifl | A61B 5/20 600/575 |
| 6,849,070 | B1 * | 2/2005 | Hansen | A61F 5/44 604/328 |
| 2003/0130646 | A1 * | 7/2003 | Kubalak | A61F 5/4404 604/544 |
| 2004/0236293 | A1 * | 11/2004 | Tanghoj | A61F 5/44 604/327 |
| 2008/0051763 | A1 * | 2/2008 | Frojd | A61M 25/0017 604/544 |
| 2008/0119803 | A1 * | 5/2008 | Lund | A61F 5/4404 604/327 |
| 2009/0163884 | A1 * | 6/2009 | Kull-Osterlin | A61M 25/002 604/328 |
| 2010/0312203 | A1 * | 12/2010 | House | A61F 5/4405 604/322 |
| 2012/0046623 | A1 * | 2/2012 | Bordeau | A61F 5/4405 604/317 |
| 2012/0116335 | A1 * | 5/2012 | Tanghoej | A61F 5/44 604/323 |

FOREIGN PATENT DOCUMENTS

| | | |
|---|---|---|
| EP | 2072075 A1 | 6/2009 |
| FR | 2942714 A1 | 9/2010 |

* cited by examiner

BAG FOR COLLECTING URINE

The invention relates to a bag for collecting urine.

Urine bags are used to collect urine when a patient is catheterised. Urine can therefore flow from the bladder, through the catheter, into the urine bag. For this purpose, a catheter can be fitted in a sustainable manner, for example, when the patient is confined to bed and urine must be diverted sustainably. A catheter can also be fitted on a short-term basis to empty the bladder once. This latter case is referred to as intermittent catheterisation which is used, for example, when a patient is paraplegic and the bladder must be emptied regularly by catheterisation or in the case of incontinence problems. Normally, intermittent catheterisation is carried out by the patient himself several times per day.

In the context of intermittent catheterisation by the patient himself in particular, comfortable handling of the urine bag before and after use is important.

For example, document EP 2 072 075 A1 describes a urine bag with an extension containing a catheter. The bag can be folded so that it can be stored by the patient in an easy and compact manner. A patient who performs intermittent self-catheterisation requires 4 to 6 catheters per day. He must consequently take several bags with included catheters in order to be independent. The bags containing a catheter are usually packaged together and the patient must handle this package or must take the bags loose. Both options present disadvantages for patients with reduced mobility.

The object of the invention is to create a urine bag that can be easily folded in order to be less bulky prior to use and that can be easily handled by a patient, in particular a paraplegic patient.

This object is solved by a urine collection bag which is formed of two sheets of plastic material that are superimposed and welded along their perimeter. The collection bag comprises a collection compartment, an intake port and an inlet into the collection compartment, said inlet being in contact with the intake port and delimiting the upper portion of said collection compartment. The intake port is equipped with a vertical extension that is closed along its perimeter and comprises a urinary catheter. The bag according to the invention is characterised in that the intake port and the inlet are offset vertically and the vertical height of the bag without the vertical extension corresponds to a multiple of the height of said extension.

A ready-for-use set of a urinary catheter and a collection bag can thus be made available to the patient, in particular for intermittent catheterisation. The urinary catheter can be placed in the extension of the bag with its distal end pointing upwards.

The ready-for-use, unused bag, with the catheter inside, can therefore be advantageously stored in a compact manner by folding the bag horizontally once or several times and by folding down the extension, then rolling it up. Usual catheters have a flat connector on their proximal end. The end of the folded bag comprising this connector can therefore be rolled in a radius which is larger than the opposite end. This gives the rolled assembly a conical shape. Several bags rolled up in this manner can be stacked one inside the other. A patient can have a sufficient stock with him for one day in a discreet manner. The bags are well protected against damage, even once they are outside their outer packaging, and are easy to handle.

The bag can preferably have a pre-cut seam on the upper end of the extension making it possible to tear the extension to the extent that the distal end of the catheter can be slid through the extension. The proximal end of the catheter remains in the extension of the bag. The connector, which is usually located on the proximal part of the catheter, can take on the function of a stop and prevents the catheter from completely coming out of the bag. The catheter can then be used in the normal manner.

The vertical height of the extension preferably represents approximately half of the total height of the bag. The bag can therefore be folded once before or after the extension with the catheter has been folded towards the bag; then the bag can be rolled up. The assembly can be easily unfolded by a patient himself, even if he has limited manual capabilities.

Advantageously, the collection bag according to the invention can be equipped with an anti-return valve at the inlet of the collection compartment which prevents a reflux of fluid in the direction of the inlet.

According to a preferred embodiment of the invention, the welded perimeter of the lower part of the collection compartment of the bag essentially corresponds to a circular section sector with an angle of at least 180°.

Due to this particular shape, the bag can stand upright once it has been filled and does not roll onto its side. The patient can place the filled bag on a flat surface, for example to get dressed, and the bag will stay there without leaking.

The angle of the essentially circular section sector of the lower part of the collection compartment of the bag can advantageously be between 180° and 330°, and in particular between 225° and 270°. The collection compartment thereby reaches its maximum width before narrowing at the top. Tests have shown that the stability of the filled bag can be improved this manner.

The shape of the lower part of the compartment can essentially be symmetrical along a vertical axis. The bag therefore narrows evenly on both sides.

The bag may present a narrowing at the level of its compartment and may widen at the top to form a vertically limited narrowing at the level of the collection compartment.

The circular part of the collection compartment preferably has volume between 350 and 550 ml and in particular 450 ml. Tests have shown that a bag having a compartment with these dimensions is stable for a content of at least about 200 ml of liquid. The volume of urine passed by a patient is usually between 200 ml and 400 ml, such that a bag according to the invention filled with this volume of liquid remains stable on a flat surface.

Advantageously, the collection compartment may have a maximum volume of approximately 750 ml. This corresponds to a maximum volume of urine passed by a patient. A bag with these dimensions therefore cannot overflow, even if the volume deposited is greater than the volume normally collected.

An exemplary embodiment of the invention is explained in more detail below by means of the appended drawings.

Figure 1:
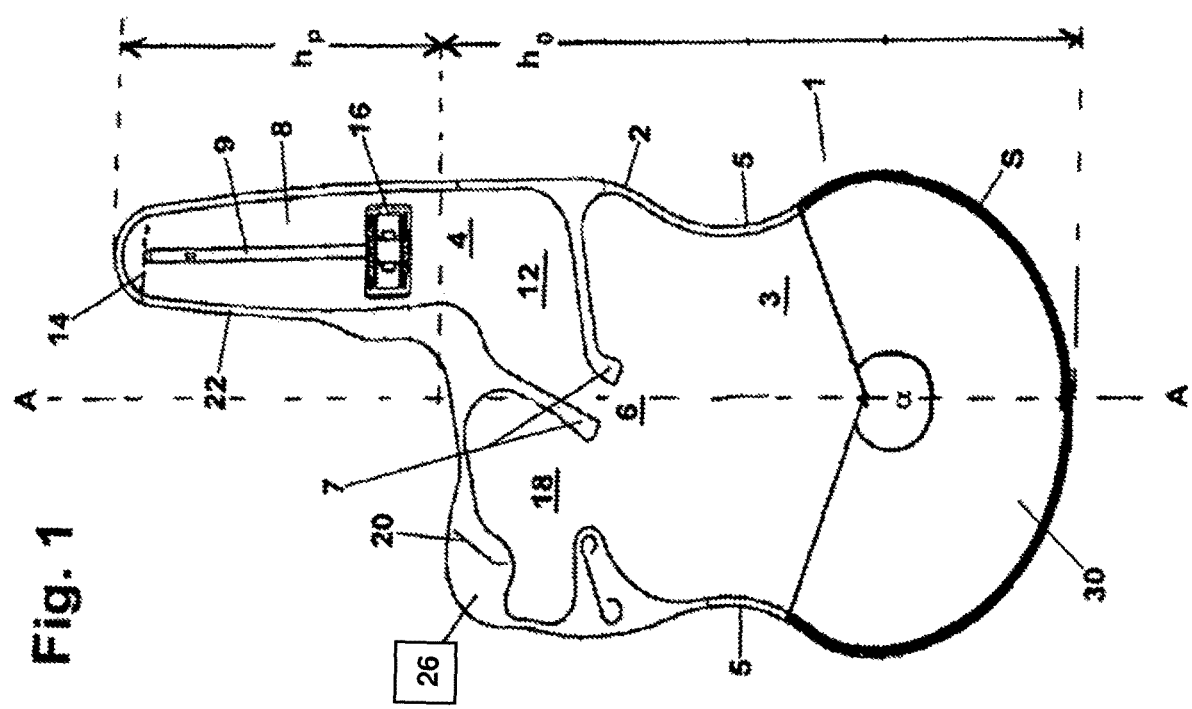
FIG. 1 represents an exemplary embodiment of a collection bag integrating a female urinary catheter.

FIG. 1 presents a preferred exemplary embodiment of a bag 1 according to the invention, designed to collect urine. A female urinary catheter 9 is integrated into the extension 8 of the bag.

The bag 1 is formed of two sheets of plastic material that are superimposed and welded along the perimeter 2 thereof.

The bag 1 comprises a collection compartment 3 to collect urine, an intake port 4 and an inlet 6 to the collection chamber 3 which is connected to the intake port 4 by a channel 12. The inlet 6 delimits the upper portion of the compartment 3.

The bag has a vertical extension 8 on its intake port 4 which is welded along its perimeter 22 such that the bag is completely closed. A female urinary catheter 9 is located in the extension 8.

The distal end of the catheter 9 can then be slid through the bag by tearing a seam 14 provided for this purpose on the end of the extension 8 and can be used in the normal manner. The proximal end of the catheter 9 with the connector 16 therefore remains inside the extension 8 such that urine can flow directly into the chamber 3 of the bag 1.

The bag 1 also has a simple anti-return valve which is formed by the two welds 7 and which prevents the reflux of liquid through the inlet 6 into the channel 12 as soon as the chamber has reached a certain filling level.

The assembly can be sterilised such that the urinary catheter 9 can be packaged to be ready for use.

The collection bag 1 has the height $h_o$ which approximately corresponds to double the height $h_p$ of the extension 8. The catheter has a flat connector 16 on its proximal end.

The bag can therefore be stored in a compact manner by firstly folding down the extension 8 with the catheter 9 and by folding the bag 1 horizontally to approximately half its height. The bag can then be rolled up.

Figure 2:
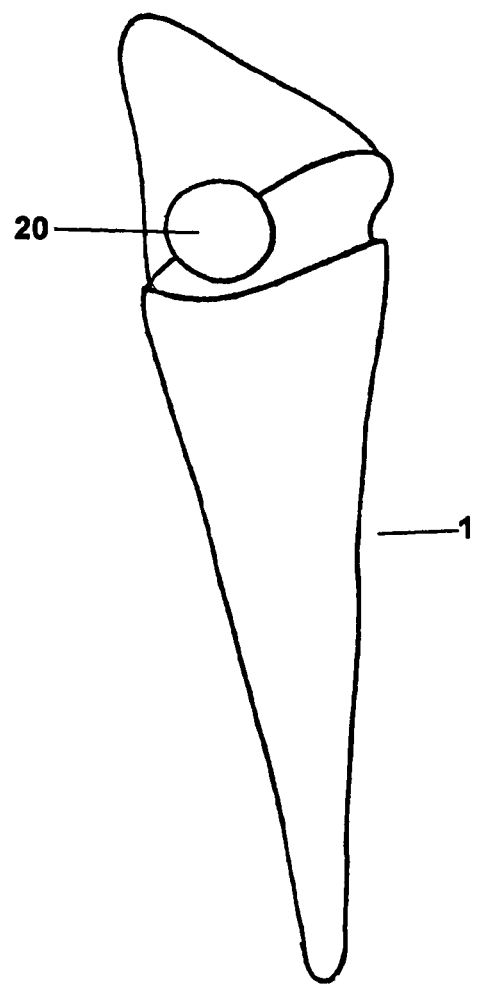
FIG. 2 represents the exemplary embodiment according to FIG. 1 in its rolled-up state.

FIG. 2 shows the bag 1 according to FIG. 1 once it has been rolled up. As one can see, a cone is created by the connector of the catheter in the extension which is folded inwards. The rolled-up bag can be fixed by a small sticker 20.

The patients can carry the rolled-up bag 1 with the catheter, which is ready for use, in a compact and discreet manner. A patient who carries out intermittent self-catheterisation requires 4 to 6 catheter per day. Given that the bags, which are rolled up in a cone shape, can be easily stacked, the patients can also easily take several bags with them. The rolled-up and stacked bags are well protected against damage, even without their outer packaging.

Returning to FIG. 1, one can see that the welded perimeter of the lower part 30 of the compartment 3 of the bag 1 essentially corresponds to a circular section S with an angle of approximately 225°. The shape of the lower part 30 of said compartment 3 is essentially symmetrical along a vertical axis A. The bag has a narrowing 5 at the level of the compartment 3.

Due to this structure of the bag, the bag can stand upright on a flat surface without tipping over with a filling level of at least about 200 ml. The bag can be deposited after use for a moment, such that, for example, the patient can get dressed or can take a sample subsequently before discarding the liquid which it contains.

The circular part of the collection compartment 3 has a volume of approximately 450 ml. Once the bladder is completely emptied, there is normally between 200 and 400 ml of urine in the chamber 3 of the bag 1. The patient can therefore put down the filled bag for a short moment to get dressed. Due to its structure according to the invention, the bag 1 remains stable, does not tip over and does not spill.

The maximum volume of the collection compartment 3 is approximately 750 ml in order to avoid any overflow in the event of there being large volumes of urine to be collected.

The bag 1 furthermore comprises an area 26 which comprises a small chamber 18 which can be opened by a tearing seam 20 in order to empty the bag.

The invention claimed is:

1. A urine collection bag (1) formed of two sheets of flexible plastic material that are superimposed and welded along a perimeter (2) thereof, said urine collection bag (1) comprising:
    a collection compartment (3);
    an intake port (4);
    an inlet (6) to the collection compartment (3), said inlet being in contact with the intake port (4) and delimiting an upper portion of said collection compartment (3),
    a closed vertical extension (8), the intake port being equipped with the closed vertical extension (8) which is closed along its perimeter (22) and comprises a pre-cut seam (14); and
    a urinary catheter (9) located in the closed vertical extension;
    wherein
    the intake port (4) and the inlet (6) are vertically offset from each other;
    a length ($h_o$) of the urine collection bag (1) without the closed vertical extension (8) corresponds to a multiple of a length ($h_p$) of said closed vertical extension (8);
    the urine collection bag (1) can be folded;
    a welded perimeter of a lower part (30) of the collection compartment (3) corresponds to a circular sector (S) with an angle (α) of at least 180° so that the urine collection bag can stand upright once it has been filled, wherein the circular sector is a lower end of the urine collection bag;
    the two sheets of flexible plastic material that are superimposed and welded along the perimeter (2) thereof define the collection compartment (3), the intake port (4), the inlet (6) and the closed vertical extension (8) so that the urine collection bag is completely closed and includes therein the urinary catheter (9);
    the urinary catheter (9) has a flat connector (16) on its proximal end; and
    the urine collection bag is in a conical shape formed by folding down the closed vertical extension (8) with the urinary catheter (9), by folding the urine collection bag horizontally to approximately half of its height and by rolling up the urine collection bag around the flat connector.

2. The urine collection bag (1) according to claim 1, wherein the length ($h_o$) of the urine collection bag (1) without the closed vertical extension corresponds to double the length ($h_p$) of the closed vertical extension (8).

3. The urine collection bag (1) according to claim 1, the urine collection bag (1) has an anti-return valve (7) at the inlet (6) of said collection compartment.

4. The urine collection bag (1) according to claim 3, wherein the anti-return valve (7) is formed by two welds (7) between the two sheets of flexible plastic material.

5. The urine collection bag (1) according to claim 1, wherein the angle (α) of the circular sector (S) is between 180° and 330°.

6. The urine collection bag (1) according to claim 1, wherein a shape of the lower part (30) of said collection compartment (3) is symmetrical along a vertical axis (A).

7. The urine collection bag (1) according to claim 1, wherein the urine collection bag has a narrowing (5) at a level of the collection compartment (3).

8. The urine collection bag (1) according to claim 1, wherein the lower part of the collection compartment (3) has a volume between 350 and 550 ml.

9. The urine collection bag (1) according to claim 1, wherein the collection compartment (3) has a maximum volume of approximately 750 ml.

10. The urine collection bag (1) according to claim 1, wherein the angle (a) of the circular sector (S) is between 225° and 270°.

11. The urine collection bag (1) according to claim 1, wherein the lower part of the collection compartment (3) has a volume of 450 ml.

\* \* \* \* \*

UNITED STATES PATENT AND TRADEMARK OFFICE
CERTIFICATE OF CORRECTION

| | |
|---|---|
| PATENT NO. | : 11,185,435 B2 |
| APPLICATION NO. | : 14/902362 |
| DATED | : November 30, 2021 |
| INVENTOR(S) | : Prezelin et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 305 days.

Signed and Sealed this
Twenty-fifth Day of February, 2025

Coke Morgan Stewart
*Acting Director of the United States Patent and Trademark Office*